United States Patent [19]

Chang

[11] 4,250,098
[45] Feb. 10, 1981

[54] CHROMOGENIC COMPOUNDS

[75] Inventor: John Chang, Fairfield, Ohio

[73] Assignee: Champion International Corporation, Stamford, Conn.

[21] Appl. No.: 928,470

[22] Filed: Jul. 27, 1978

[51] Int. Cl.³ .......................................... C07D 493/10
[52] U.S. Cl. ................................. 260/335; 252/316; 428/307; 428/914; 282/27.5
[58] Field of Search ........................................ 260/335

[56] References Cited

U.S. PATENT DOCUMENTS 4,104,437  8/1978  Vincent et al. ..................... 428/307

FOREIGN PATENT DOCUMENTS 47-20479  6/1972  Japan .

OTHER PUBLICATIONS

Chemical Abstracts, vol. 77, (1972), 153918v.

Primary Examiner—Norma S. Milestone
Attorney, Agent, or Firm—Evelyn M. Sommer

[57] ABSTRACT

A chromogenic compound having the structural formula

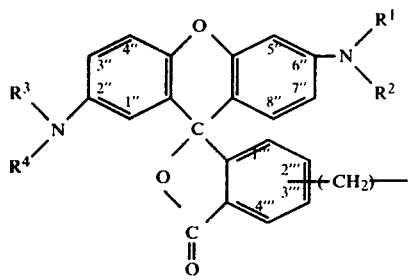

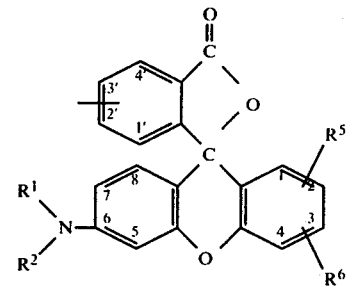

wherein
$R^1$, $R^2$, $R^3$, $R^4$ and $R^6$ represent hydrogen, an alkyl group, a benzyl group or an aryl group;
$R^5$ represents hydrogen, an alkyl group, a benzyl group, an aryl group or Y, wherein
Y represents

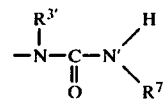

and
$R^{3'}$ and $R^7$ represent hydrogen, an alkyl group, a benzyl group or an aryl group;
with the proviso that when $R^5$ represents Y, $R^6$ represents hydrogen and Y is at the 2 position, and
n is an integer of 1 to 6.

The aforesaid compound may be provided in a pressure-sensitive copy system wherein a visible image is formed upon reaction of the above chromogenic compound with an electron-accepting material of the Lewis acid type to produce a black image.

6 Claims, No Drawings

CHROMOGENIC COMPOUNDS

This invention relates to chromogenic compounds, the production of such compounds, and to pressure-sensitive copy systems employing such compounds. More particularly, this invention relates to substantially colorless, single component, substituted di-fluoran chromogenic compounds which are converted to a visible black image when placed in reactive contact with a Lewis acid material, such as acid clay, the production of such compounds and to pressure-sensitive copy systems wherein such compounds are enclosed in microcapsules.

Numerous marking systems have been suggested which involve localized contact between a chromogenic compounds and a color-developing substance in areas where a colored marking is desired. Pressure-sensitive mark-forming systems are described, for example, in U.S. Pat. Nos. 3,418,656 and 3,418,250 to A. E. Vassiliades and U.S. Pat. No. 3,875,074 to Vassiliades et al. These patents describe a marking system wherein a substantially colorless chromogenic substance is disposed in minute oil droplets within microcapsules, the walls of which form pressure-rupturable barriers. The microcapsules are coated onto a substrate which is superimposed onto a receiving sheet, which is coated with an electron-accepting material of the Lewis acid type, such as an acid-treated clay. Upon application of localized pressure to the opposite side of the microcapsule-coated sheet, the microcapsules are ruptured and the colorless chromogenic substance is released for reaction with the acidic co-reactant to provide a distinctive mark.

In such pressure-sensitive copying papers, a plurality of different chromogenic compounds are normally needed to formulate a black imaging system. Such multicomponent dye systems have several disadvantages. For example, the initial image may develope in various hues during the first few minutes since the dyes have their individual reactivities towards the coreactant in the receiving sheet. Additionally, such image may fade to a different color on aging depending upon the stability of each chromogen. Moreover, careful color matching is normally required for such systems, and the dye purity is critical in obtaining a proper combination.

In accordance with the present invention, single component, substantially colorless, chromogenic compounds capable of providing a visible, black image are provided, said compounds having the structural formula

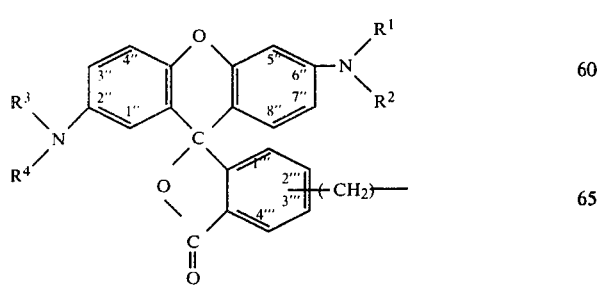

-continued

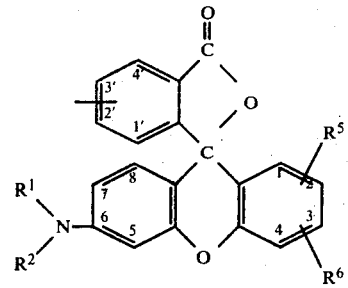

wherein
$R^1$, $R^2$, $R^3$, $R^4$ and $R^6$ represent hydrogen, an alkyl group, a cycloalkyl, a benzyl group or an aryl group;
$R^5$ represents hydrogen, an alkyl group, a benzyl group, an aryl group or Y, wherein
Y represents

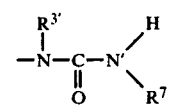

and
$R^{3'}$ and $R^7$ represent hydrogen, an alkyl group, a benzyl group or an aryl group,
with the proviso that when $R^5$ represents Y, $R^6$ represents hydrogen and Y is at the 2 position; and
n is an integer of 1 to 6.

The substantially colorless di-fluoran chromogenic compounds of the present invention are converted to a black coloration upon contact with an acidic color-reacting substance, e.g., a Lewis acid material such as acid clay, a phenolic resin, or a carboxylic acid of the type described in U.S. Pat. No. 3,488,207 to Vassiliades. The black markings provided by the chromogenic compounds of the present invention will possess excellent stability upon exposure to light.

Preferrably the single component, chromogenic compounds of the present invention have the structural formula set forth above wherein;
$R^1$ and $R^2$ each represent a lower alkyl group having 1 to 5 carbon atoms, e.g., methyl, ethyl, propyl, butyl, amyl;
$R^3$ and $R^4$ each represent hydrogen, a lower alkyl having 1 to 5 carbon atoms, e.g., methyl, ethyl, propyl, butyl, amyl; a benzyl group, or a phenyl group;
$R^5$ represents hydrogen, a lower alkyl having 1 to 5 carbon atoms, e.g., methyl, ethyl, propyl, butyl, amyl; a benzyl group, a phenyl group, or Y, wherein
Y represents

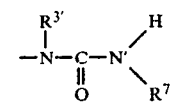

and
$R^{3'}$ represents hydrogen, a lower alkyl group having 1 to 5 carbon atoms, e.g., methyl, ethyl, propyl, butyl, amyl; a benzyl group, or a phenyl group, and $R^7$ represents a lower alkyl group having from 1 to 5 carbon atoms, e.g., methyl, ethyl, propyl, butyl, amyl; a benzyl group, or an aryl group, with the proviso that when $R^5$ represents Y, $R^6$ represents hydrogen and Y is at the 2 position;

$R^6$ represents hydrogen, a lower alkyl group having 1 to 5 carbon atoms, e.g., methyl, ethyl, propyl, butyl, amyl; a benzyl group or a phenyl group; and n is an integer from 1 to 6.

Especially preferred single component, chromogenic compounds of the present invention have the structural formula

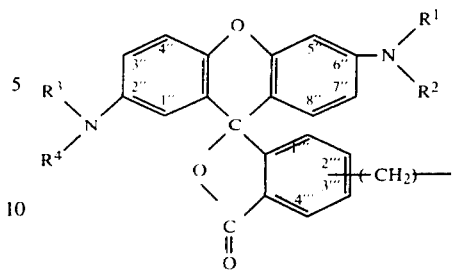

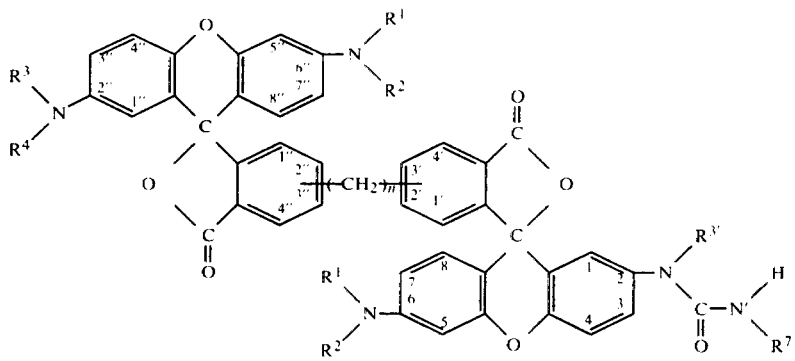

wherein
$R^1$, $R^2$, $R^3$, $R^{3'}$ and $R^7$ each represent hydrogen, a lower alkyl group having from 1 to 5 carbon atoms, e.g., methyl, ethyl, propyl, butyl, amyl; a benzyl group or an aryl group; and n is an integer from 1 to 6.

Chromogenic compounds having this general structure are referred to herein as alkylene bridged fluoran-ureidofluorans due to the presence of a substituted ureido group thereon.

Another set of especially preferred single component, chromogenic compounds of the present invention, referred to herein as alkylene bridged di-fluorans, have the structural formula

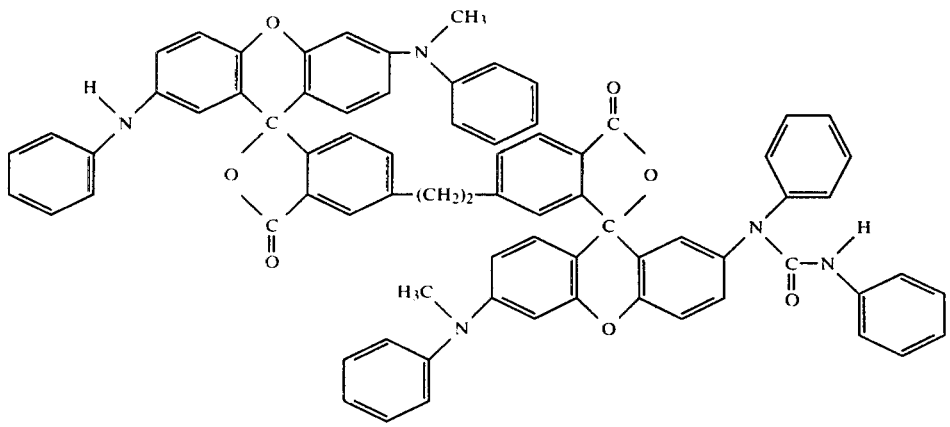

wherein
$R^1$, $R^2$, $R^3$, $R^4$, $R^5$ and $R^6$ each represent hydrogen, a lower alkyl group having from 1 to 5 carbon atoms, e.g. methyl, ethyl, propyl, butyl, amyl; a benzyl group or an aryl group; and n is an integer from 1 to 6.

Examples of the single component, chromogenic compounds of the present invention include:

2',3'''-ethylene-[2-(N'-phenyl-N-phenylureido)-6-methylphenyl-amino-2''-phenylamino-6''-methylphenylamino] difluoran -continued

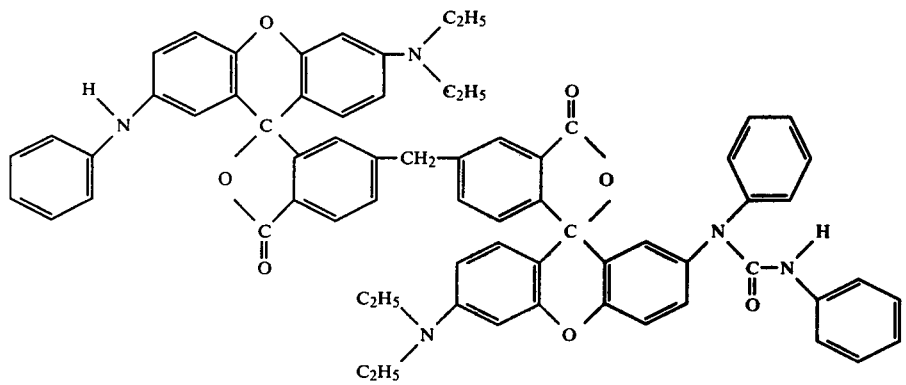

2''',3'-methylene-[2-(N'-phenyl-N-phenylureido)-6-diethyl-amino-2''-phenylamino-6''-diethylamino] difluoran

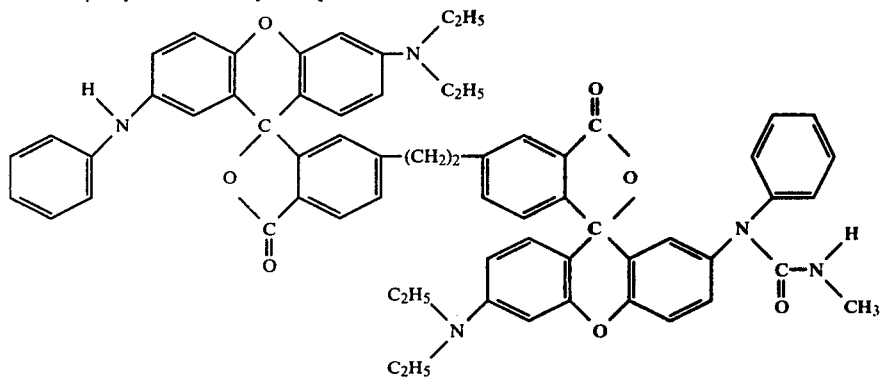

2''',3'-ethylene-[2-(N'-methyl-N-phenylureido)-6-diethyl-amino-2''-phenylamino-6''-diethylamino] difluoran

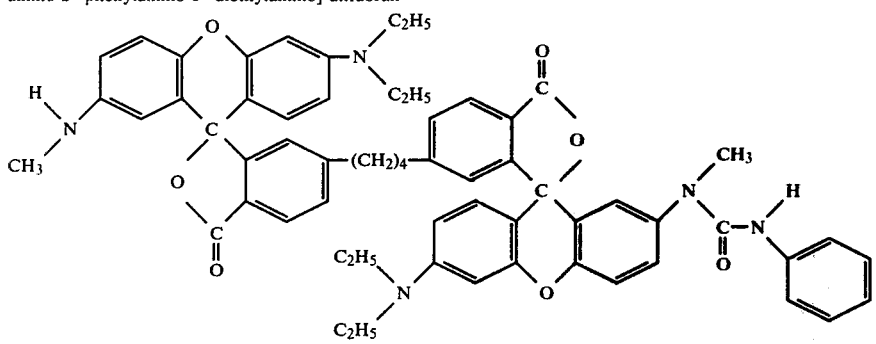

2',2'''-tetramethylene-[2-(N'-phenyl-N-methylureido)-6-diethyl-amino-2''-methylamino-6''-diethylamino] difluoran

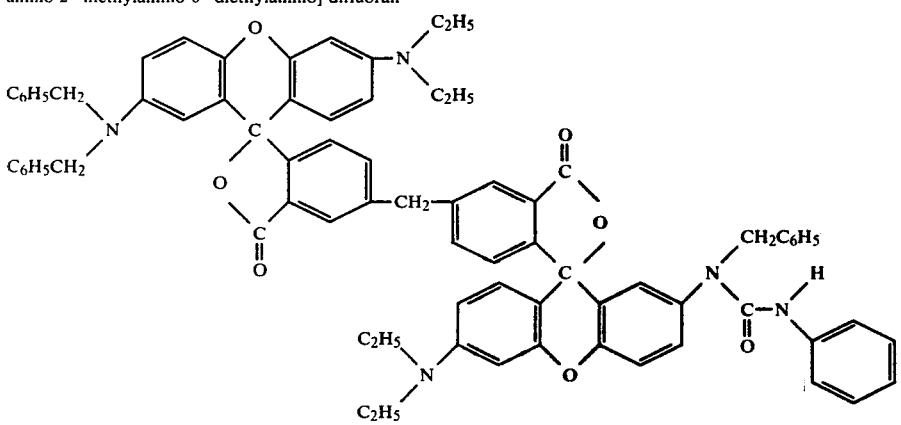

3',3'''-methylene-[2-(N'-phenyl-N-benzylureido)-6-diethyl-amino-2''-dibenzylamino-6''-diethylamino] difluoran

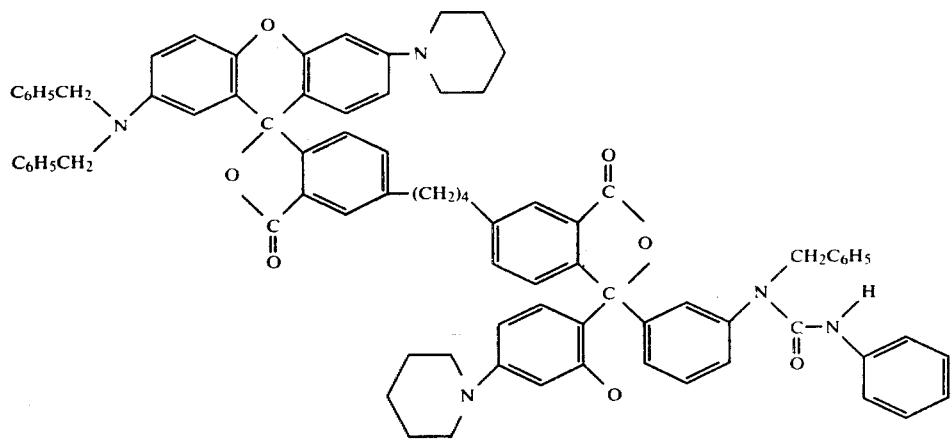

3',3'''-tetramethylene-[2-(N'-phenyl-N-benzylureido)-6-
(α-piperidyl)-2''-dibenzylamino-6''-(α-piperidyl)] difluoran

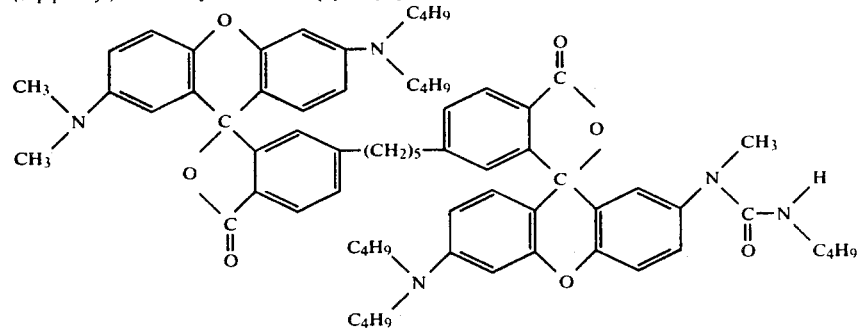

2',2'''-pentamethylene-[2(N'-butyl-N'-methylureido)-6-dibutyl-
amino-2''-dimethylamino-6''-dibutylamino] difluoran

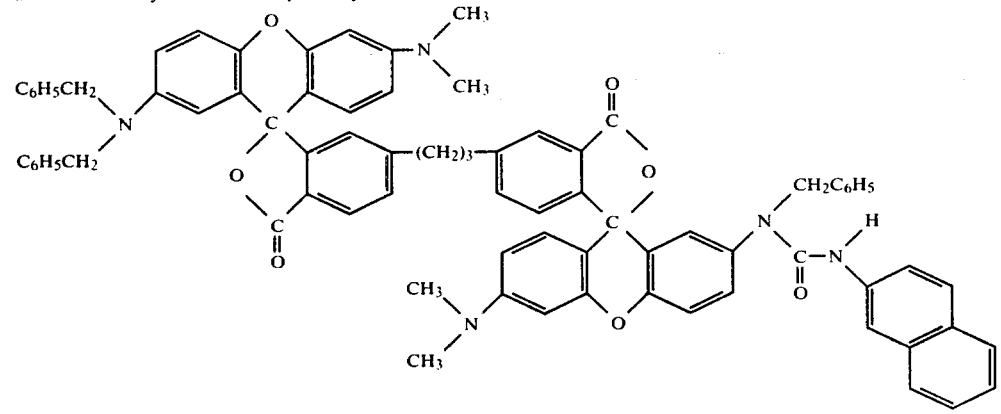

2''',3'-trimethylene-[2-(N'-(β-naphthyl)-N-benzylureido)
6-dimethylamino-2''-dibenzylamino-6''-dimethylamino]diflouran

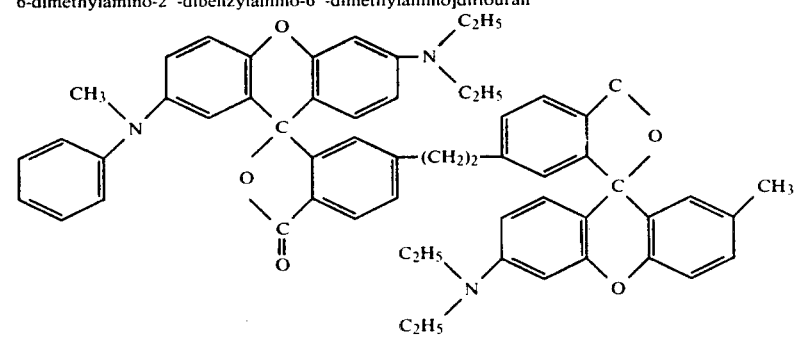

2', 2'''-ethylene-[2-methyl-6-diethylamino-2''-methylphenyl-
amino-6''diethylamino]difluoran

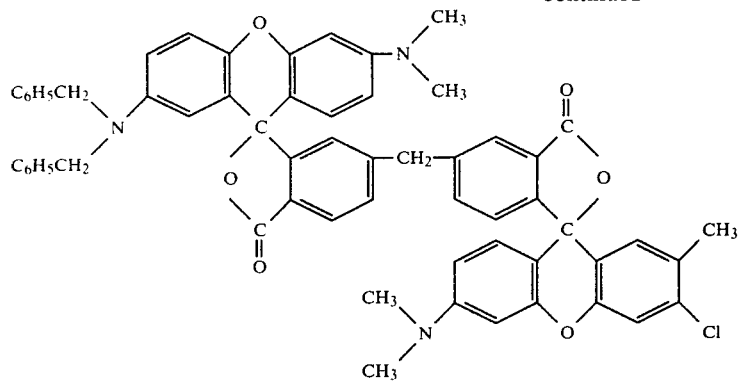

2′′′,3′-methylene-[2-methyl-3-chloro-6-dimethylamino-2′′-dibenzylamino-6′′-dimethylamino]difluoran

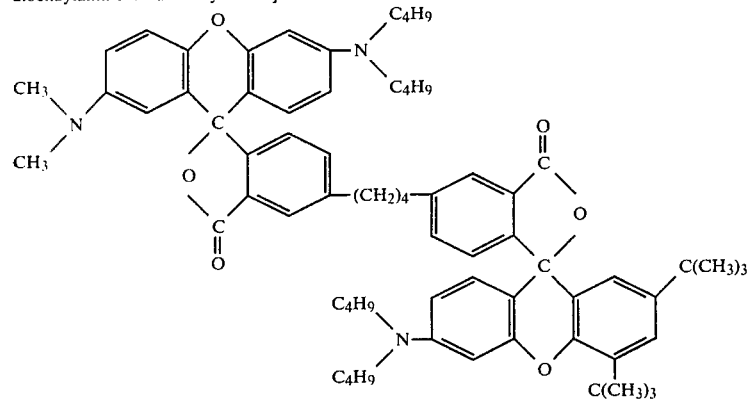

3′,3′′′-tetramethylene-[2,4-di-tert-butyl-6-dibutylamino-2′′-dimethylamino-6′′-dibutylamino]difluoran

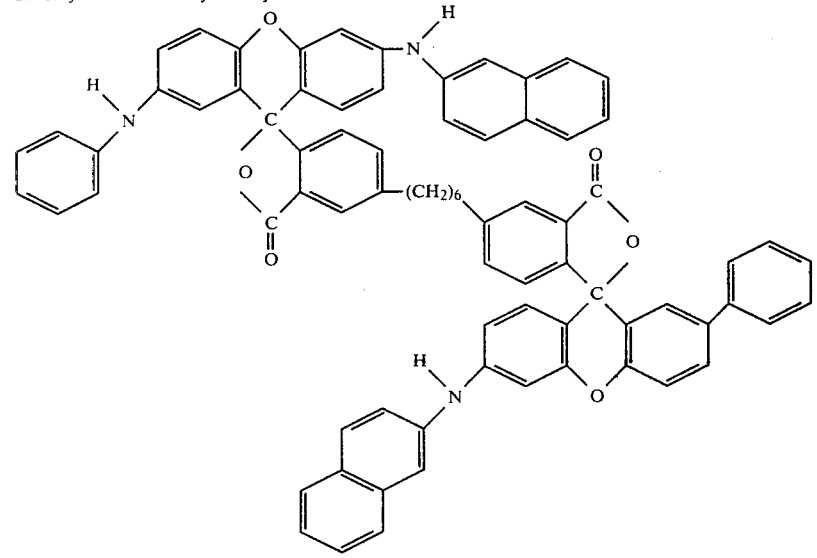

3′,3′′′-hexamethylene-[2-phenyl-6-(β-naphthylamino)-2′′-phenylamino-6′′-(β-naphthyl)]difluoran According to the present invention, the single component, chromogenic compounds of the present invention are produced by reacting an alkylene bridged diphthalic anhydride with a m-amino phenol to produce an alkylene bridged bis-(2′-carboxy-4-amino-2-hydroxybenzophenone), wherein n is an integer from 1 to 6, as follows:

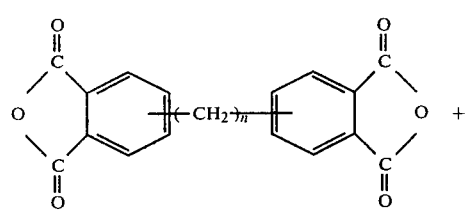

(I)

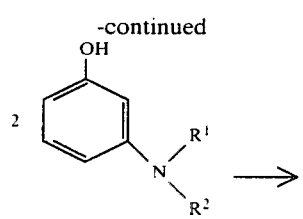

To obtain the alkylene bridged, fluoran-ureidofluoran compounds of the present invention (those compounds wherein $R^5=Y$ and $R^6=H$), first, the resulting reaction (I) product is reacted with two moles of a substituted p-aminophenol to produce the precursor alkylene bridged, fluoran-ureidofluoran as follows:

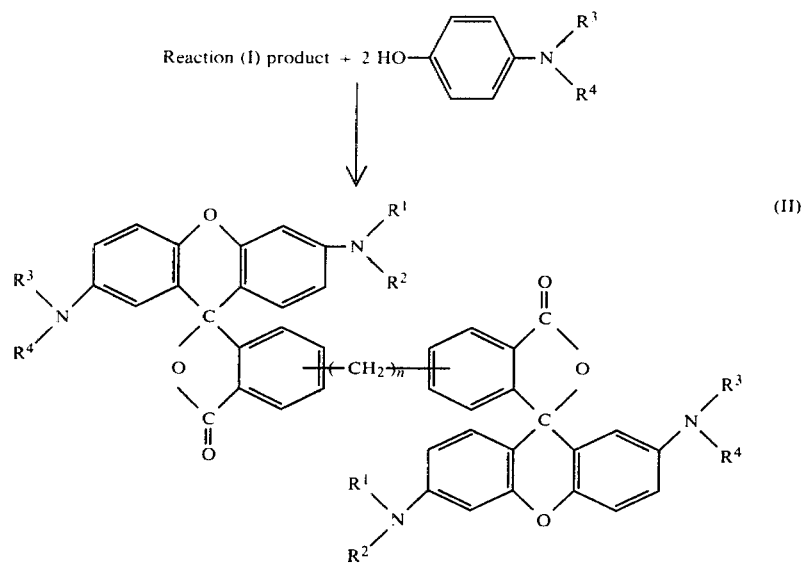

According to another aspect of the present invention, one mole of the resulting precursor alkylene bridged, fluoran-ureidofluoran is then reacted with one half mole of an isocyanate to produce the alkylene bridged fluoran-ureidofluoran compounds of the present invention (where $R^5=Y$ and $R^6=H$) as follows:

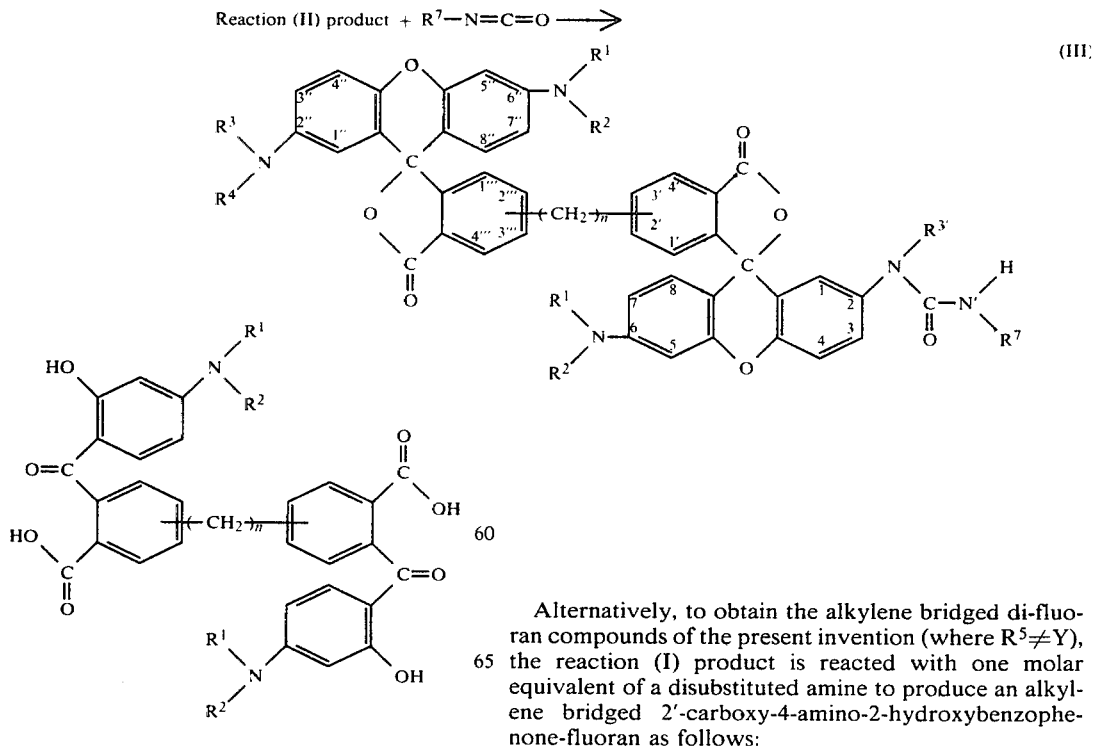

Alternatively, to obtain the alkylene bridged di-fluoran compounds of the present invention (where $R^5 \neq Y$), the reaction (I) product is reacted with one molar equivalent of a disubstituted amine to produce an alkylene bridged 2'-carboxy-4-amino-2-hydroxybenzophenone-fluoran as follows:

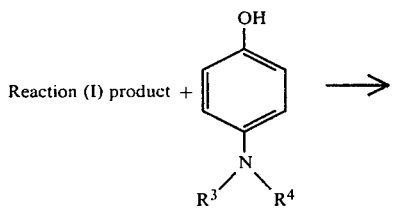

wherein R³ and R⁴ represent hydrogen, an alkyl group, a benzyl group or an aryl group.

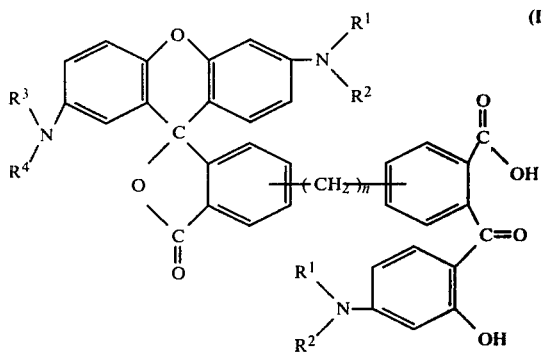

Thereafter, the resulting reaction (IV) product is reacted with a phenol to produce the subject alkylene bridged di-fluoran compounds as follows:

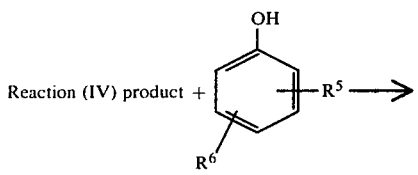

wherein R⁵ and R⁶ represent hydrogen, a lower alkyl group, a benzyl group or an aryl group.

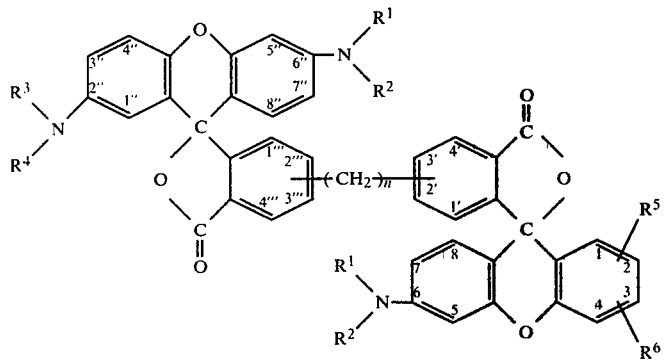

Reaction II may be conducted under acidic conditions, e.g., in the presence of sulfuric or phosphoric acid, at a temperature, for example, in the range of between about 10° and about 60° C., preferably between about 20° and about 40° C., under atmospheric pressure conditions, for a period of, for example, between about 2 and about 80 hours, preferably between about 6 and about 65 hours. In the foregoing reactions, $R^1$, $R^2$, $R^3$, $R^{3'}$, $R^4$, $R^5$, $R^6$, $R^7$, and Y are defined as previously indicated. Accordingly, the isocyanate employed in Reaction III may be any isocyanate having the formula $R^7$—N=C=O, such as methyl isocyanate, ethyl isocyanate, t-butyl isocyanate, β-naphthylisocyanate, phenyl isocyanate, benzyl isocyante, 4-chlorophenyl isocyanate, and the like. Reaction III may be conducted, for example, at a temperature in the range of between about 40° and about 150° C. for a period of between about 2 and about 10 hours.

The alkylene bridged, fluoran-ureidofluoran reaction products of the present invention formed in Reaction III may be washed with water, precipitated out in heptane, and dried to produce a substantially colorless solid product which becomes black in color upon contact with a Lewis acid material.

According to a further aspect of the present invention, the single component, chromogenic compounds of the present invention may be dissolved in an oily solvent such as dialkylnaphthalene, cottonseed oil, coconut oil, a chlorinated biphenyl, or the like, and encapsulated for use in a carbonless copy system.

Any suitable process may be utilized for forming the microcapsules and the copy sheets bearing such microcapsules including those processes described in U.S. Pat. Nos. 3,418,250 and 3,418,656, the disclosures of which are hereby incorporated by reference. The resultant microcapsules may be coated on or incorporated in a web or substrate, such as paper, and utilized in any form of pressure-sensitive copy system wherein the microcapsules are ruptured under localized pressure to release the single component for contact with an acidic co-reactant. Thus, for example, the microcapsule-bearing substrate may be also coated with the acidic, co-reactant, such as an acidic clay. Such system is normally referred to as a "self-contained" or "autogenous" system, since the colorless chromogenic material and the acidic, co-reactant are present on the same substrate.

Alternatively, the microcapsules containing the single component, chromogenic compounds of the present invention may be coated onto and/or incorporated into a substrate which is used in combination with a separate sheet or substrate which contains the acidic co-reactant. This type of copy system is normally referred to as a "transfer copy system", and upon rupture of the capsules by localized pressure the chromogen contacts a separate acid-coated sheet upon which a black mark is thereby provided. Accordingly, the colorless chromogens of the present invention may be utilized in any copy system where they are isolated from the acidic co-reactant prior to the formation of the desired black image.

According to another aspect of the present invention, the single component, chromogenic compounds of the present invention are employed in pressure-rupturable copy systems wherein said compounds are enclosed in microcapsules that are formed by a reaction involving a poly-functional isocyanate. The preferred system for forming microcapsules involving the fluoran compounds of the present invention is described in U.S. Pat. No. 3,875,074 to A. E. Vassiliades et al, the disclosure of which is hereby incorporated by reference. According to the system described therein, pressure-rupturable oil-containing microcapsules are provided by admixing:

(A) A water-immiscible, oily material containing the single component, chromogenic compound of the present invention and an oil-soluble, non-polymeric cross-linking agent in the form of a poly-functional isocyanate; and (B) An aqueous solution of an organic, polymeric emulsifying agent containing a plurality of hydroxyl groups.

The water-immiscible oily material and the aqueous solution of the emulsifying agent are admixed under conditions to form an oil-in-water emulsion, wherein the oily material is dispersed in the form of microscopic emulsion droplets in an aqueous, continuous phase. The emulsifying agent aids in the formation of the emulsion and additionally, possesses cross-linkable hydroxyl groups that are capable of reacting with the cross-linking agent to form a cross-linked capsule wall at the oil/water interface. The cross-linking agent is reacted with the hydroxyl groups of the polymeric emulsifying agent and in such manner surrounds each of the droplets with a solid, cross-linked capsule wall.

The preferred oil-soluble poly-functional isocyanates are 4,4'-diphenylmethane diisocyanate, toluene diisocyanate, hexamethylene diisocyanate, triphenylmethane triisocyanate, mixtures of such isocyanates, and adducts of such isocyanates with polyhydric alcohols, such as trimethylolpropane. A preferred isocyanate cross-linking agent is an adduct of toluene diisocyanate with glycerol (3:1 molar), pentaerythritol (4:1 molar), hexanetriol (3:1 molar) or trimethylolpropane (3:1 molar). An especially preferred isocyanate cross-linking agent is the adduct of toluene diisocyanate and trimethylol propane.

The film-forming polymeric emulsifying agent may be a poly-hydroxyl group-containing polymer, such as polyvinyl alcohol, methylcellulose, a benzylated starch or the like.

As previously indicated, the single component, chromogenic compounds of the present invention provide a black image upon contact with the electron-accepting Lewis acid material. Any of the well-known acidic materials including bentonite, kaolin, acidic clays, talc, aluminum silicate, calcium citrate, metal oxides, metal chlorides or the like.

Various concentrations of the single component, chromogenic compounds of the present invention may be utilized in the formation of chromogen-containing microcapsules for use in copy systems. Thus, for example, the chromogens can be used in amounts of between about 1 and about 6 parts by weight per 100 parts by weight of the oily core material of the microcapsules. Preferably, between about 2 and about 4 parts by weight per 100 parts by weight of oil may be used. Larger amounts of the chromogen may be utilized, if desired. However, relatively small amounts of the chromogens develop a high intensity black image. Suitable amounts of the chromogens may be easily determined experimentally for each particular system.

The single component, chromogenic compounds of the present invention may also be used in combination with other colorless chromogenic compounds. For example, the precursor fluoran compound mentioned before, crystal violet lactone (CVL), and benzoyl leuco methylene blue (BLMB) may be added to provide an excellent black imaging system. The total quantity of the dyes per 100 parts by weight of the oily core material of the microcapsules can be in amounts of between about 2 and 8 parts by weight, while the molar ratio of ureido fluoran:precursor fluoran:CVL:BLMB can be, for example, 2.0:3.0:0.1:0.2. Preferably, between about 4 and 6 parts by weight per 100 parts by weight of oil may be used.

The invention will be further illustrated by the following examples. The percentages are by weight unless otherwise specified.

EXAMPLE I

Preparation of isomeric methylene-bis(2'-carboxy-4-diethylamino-2-hydroxy benzophenone)—reaction I product One mole of methylene diphthalic anhydride and two moles of m-diethyl-aminophenol are dissolved in an aprotic solvent, such as benzene, xylene, and chlorobenzene and heated at about 60° to 150° C. for about 2 to 24 hours. The reaction mixture is then allowed to cool to room temperature and filtered to collect the crude solid product which is further washed with methanol or chloroform. This product can be purified by conventional recrystallization process or by dissolving the solid in an alkaline solution followed by neutralization to precipitate the product.

EXAMPLE II

Preparation of 2''',3'-methylene-bis(2-anilino-6-diethylaminofluoran) and its isomers—reaction II product One mole of the product obtained in Example I is dissolved in concentrated sulfuric acid at ambient temperature. The solution is kept at a temperature of about 40° C. or lower, while two moles of p-anilinophenol are being slowly added under agitation. The agitation is continued for about 10 to 60 hours at ambient temperature. The solution is gradually poured into a mixture of ice and excess amount of alkaline base solution, such as sodium hydroxide and potassium hydroxide. The resulting mixture is extracted with an aprotic solvent, such as benzene, toluene, xylene, and chlorobenzene. The extract is washed with water until the washings are neutral. The desired product is precipitated out by stirring the extract into aliphatic hydrocarbon solvents.

EXAMPLE III

Preparation of methylene-[2-(N'-phenyl-N-phenylureido)-6-diethylamino-2''-phenylamino-6''-diethylamino] difluoran and its isomers—reaction III product One mole of the product obtained in Example II is dissolved in a dry aprotic solvent, such as benzene, toluene, and xylene. One mole of phenyl isocyanate is added to the solution. The resulting solution is heated at about 40° to 140° C. for about 1 to 24 hours. Upon cooling to the room temperature, the solution is slowly poured into an aliphatic hydrocarbon solvent to precipitate the product.

EXAMPLE IV

Preparation of 3',3'''-tetramethylene-[2,4-di-tert-butyl-6-dibutylamino-2''-dimethylamino-6''-dibutylamino] difluoran and its isomers—reaction V product The reaction I intermediate is prepared by following the procedure of Example I with the exception that m-dibutylamino phenol and tetramethylene diphthalic anhydride are used instead of m-diethylaminophenol and methylene diphthalic anhydride; repsectively. One mole of this intermediate is reacted with one mole of p-dimethylaminophenol according to the procedure of Example II. The product obtained is further reacted with an equal molar equivalent of 2,4-di-tert-butylphenol in a concentrated sulfuric acid, 70 to 95% by weight, at about 70° to 120° C. for about 1 to 5 hours. After cooling to the room temperature, the reaction mixture is slowly poured into the mixture of ice and excess amount of alkaline base solution, such as sodium hydroxide or potassium hydroxide. The resulting mixture is extracted with an aprotic solvent. The extract is washed with water until the washings are neutral. The product is finally precipitated out by adding the extract into aliphatic hydrocarbon solvents.

This invention has been described in considerable detail with particular reference to preferred embodiments, but it will be understood that variations and modifications can be effected within the spirit and scope of the invention as described in the appended claims.

What is claimed is:

1. A chromogenic compound represented by the formula

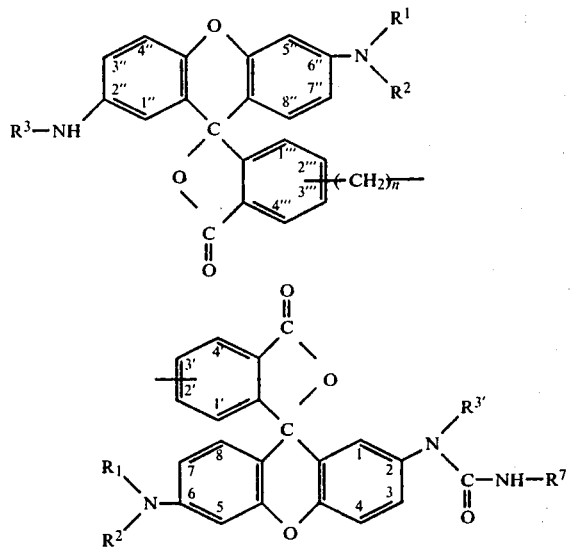

wherein
each of $R^1$ and $R^2$ represents alkyl having 1 to 5 carbon atoms, or phenyl,
$R^3$ and $R^{3'}$ are the same and represent alkyl having 1 to 5 carbon atoms, benzyl or phenyl,
$R^7$ represents alkyl having 1 to 5 carbon atoms, or phenyl,
the alkylene bridging group $(CH_2)_n$ is attached to either the 2' or 3' position and either to the 2''' or 3''' position, and
n is an integer from 1 to 6.

2. The chromogenic compound of claim 1 wherein $R^1$ and $R^2$ each represent alkyl having 1 to 5 carbon atoms.

3. A chromogenic compound in accordance with claim 1 represented by the formula:

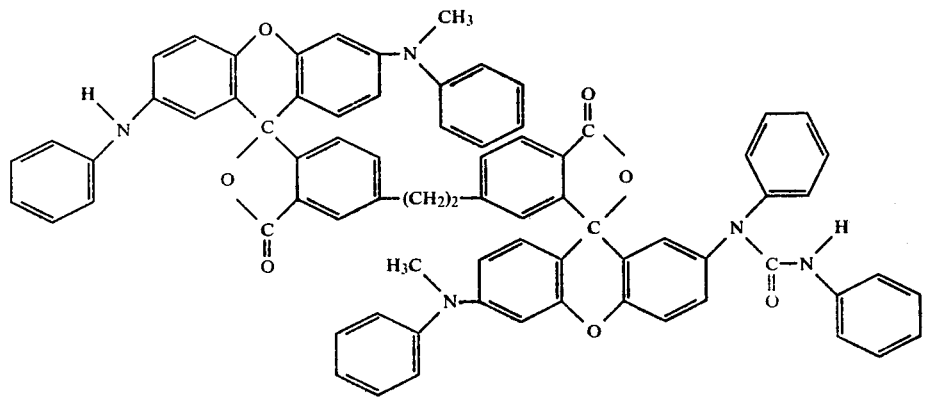

4. A chromogenic compound in accordance with claim 2 represented by the formula:

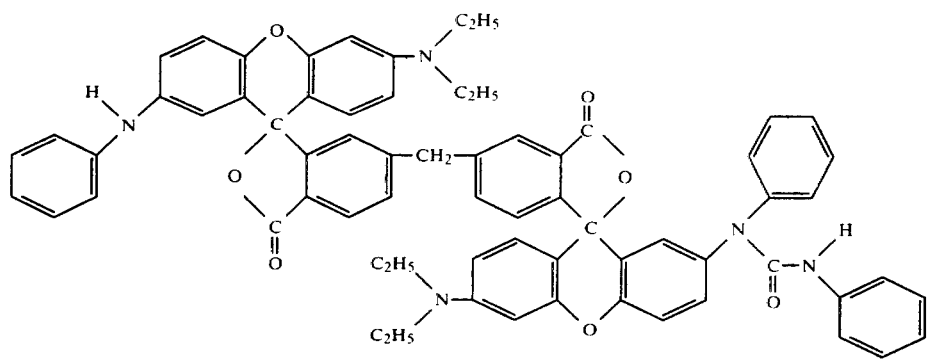
5. A chromogenic compound in accordance with claim 2 represented by the formula:
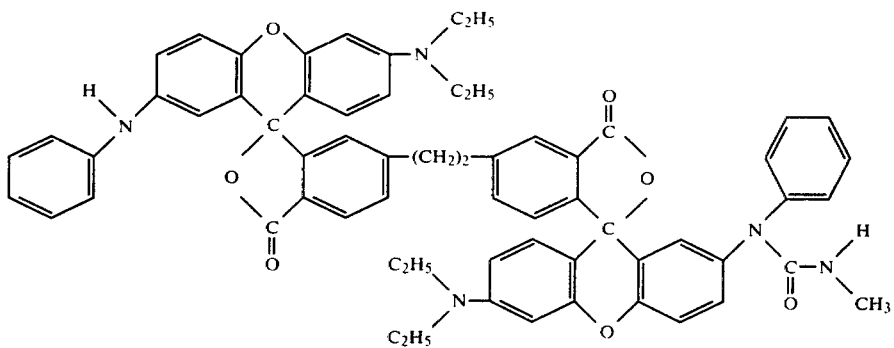
6. A chromogenic compound in accordance with claim 2 represented by the formula:
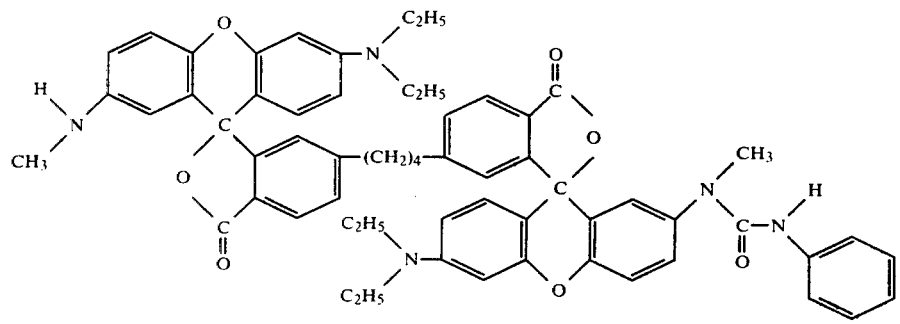
* * * * *

UNITED STATES PATENT AND TRADEMARK OFFICE
CERTIFICATE OF CORRECTION

PATENT NO. : 4,250,098  Page 1 of 4
DATED : February 10, 1981
INVENTOR(S) : John Chang It is certified that error appears in the above—identified patent and that said Letters Patent is hereby corrected as shown below:

In the Abstract, please correct the formula to read:

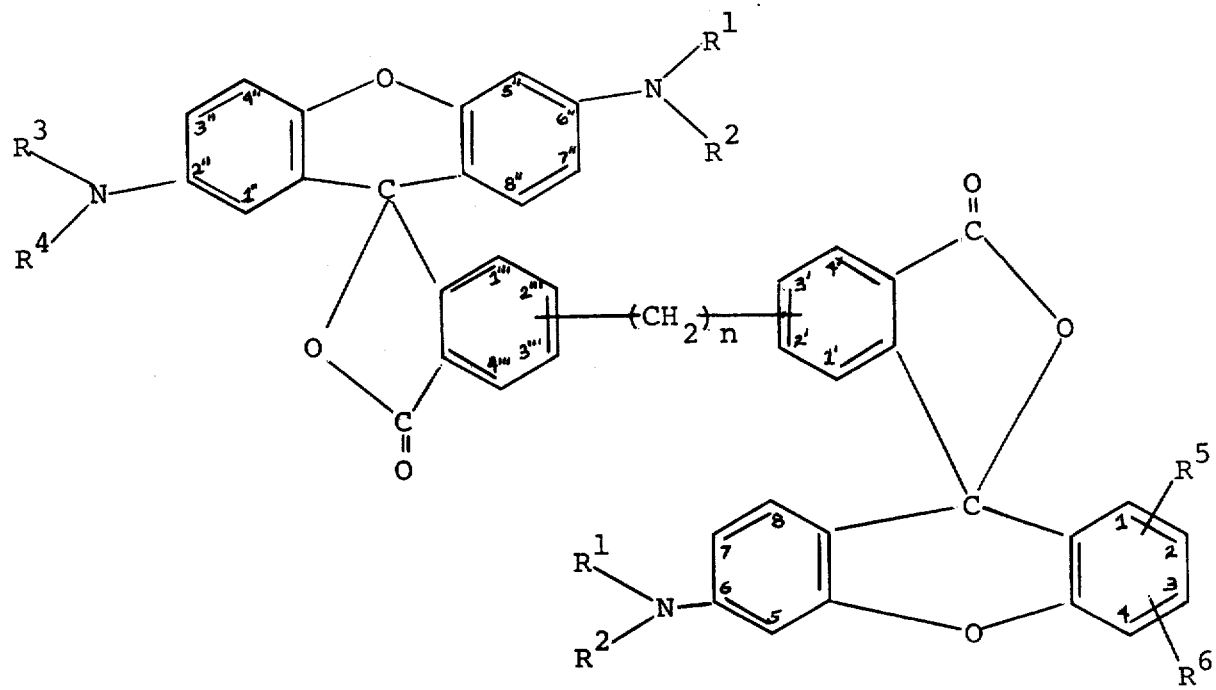

Column 3, line 30, after "$R^3$" insert -- , $R^4$ --.

UNITED STATES PATENT AND TRADEMARK OFFICE
CERTIFICATE OF CORRECTION

PATENT NO. : 4,250,098

DATED : February 10, 1981

INVENTOR(S) : John Chang

It is certified that error appears in the above—identified patent and that said Letters Patent is hereby corrected as shown below:

In Column 1, lines 56-68, please correct the formula to read:

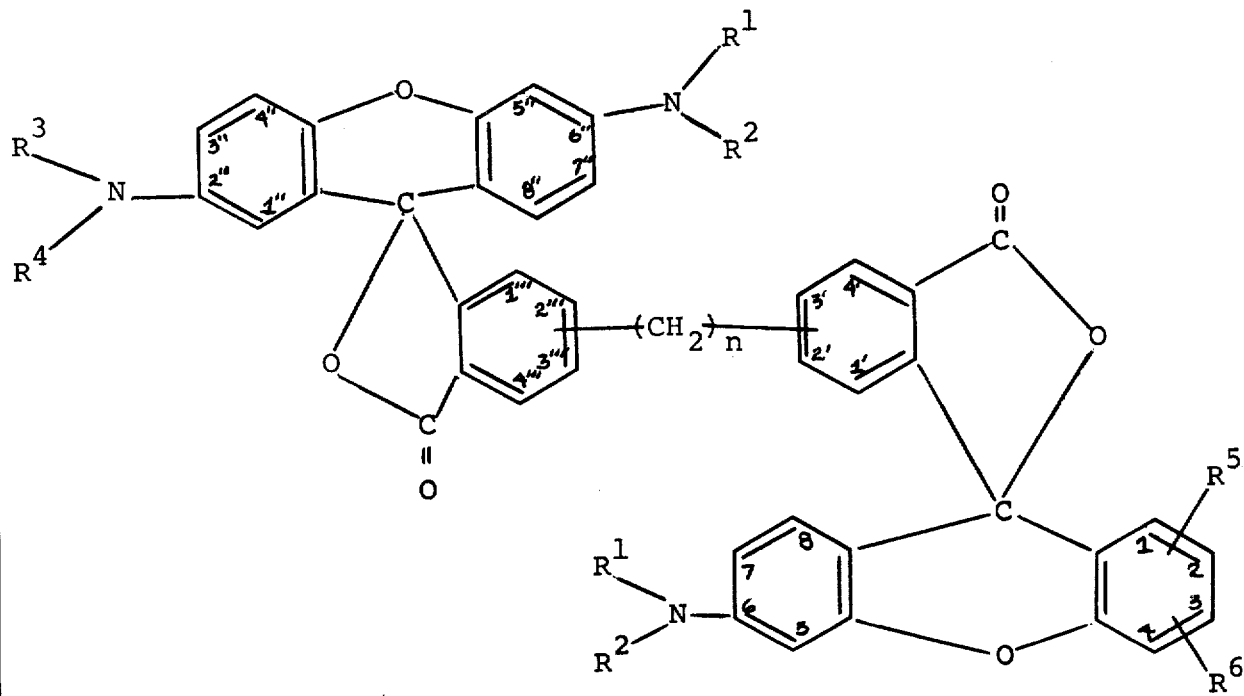

UNITED STATES PATENT AND TRADEMARK OFFICE
CERTIFICATE OF CORRECTION

PATENT NO. : 4,250,098

DATED : February 10, 1981

INVENTOR(S) : John Chang

Page 3 of 4

It is certified that error appears in the above—identified patent and that said Letters Patent is hereby corrected as shown below:

Column 4, lines 1-12, please correct the first formula to read:

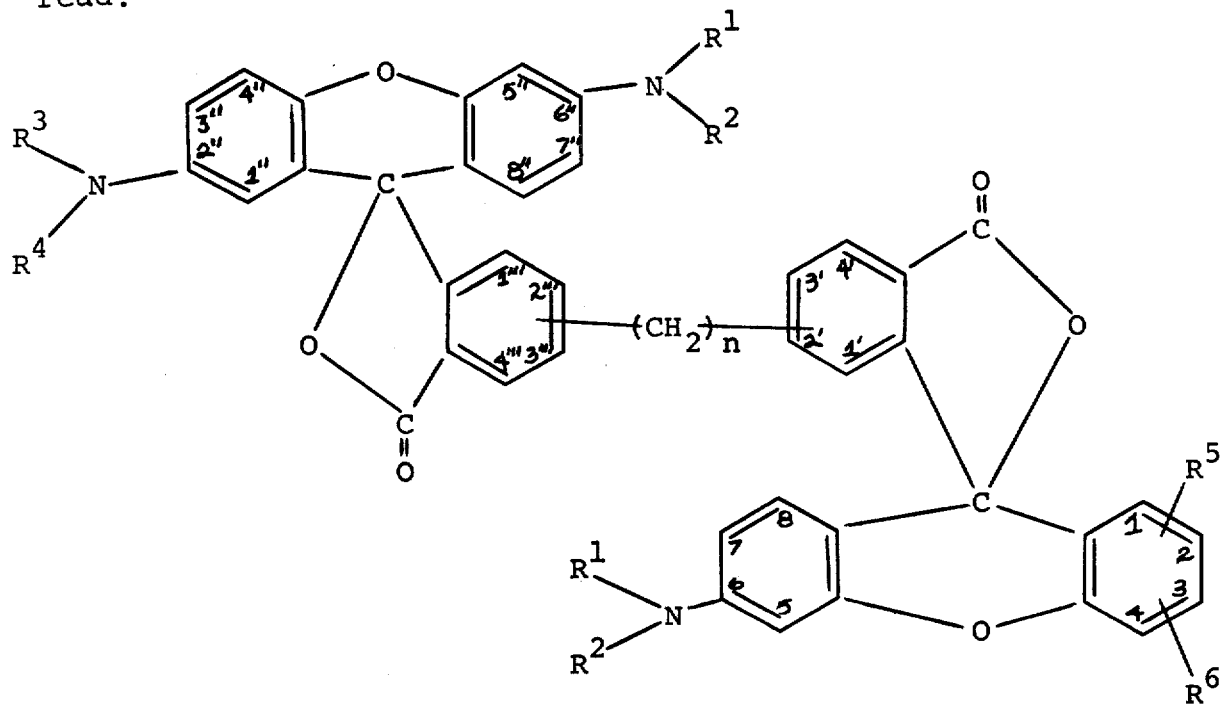

UNITED STATES PATENT AND TRADEMARK OFFICE
CERTIFICATE OF CORRECTION

PATENT NO. : 4,250,098
DATED : February 10, 1981
INVENTOR(S) : John Chang

It is certified that error appears in the above—identified patent and that said Letters Patent is hereby corrected as shown below:

In Column 7, please correct the last formula to read:

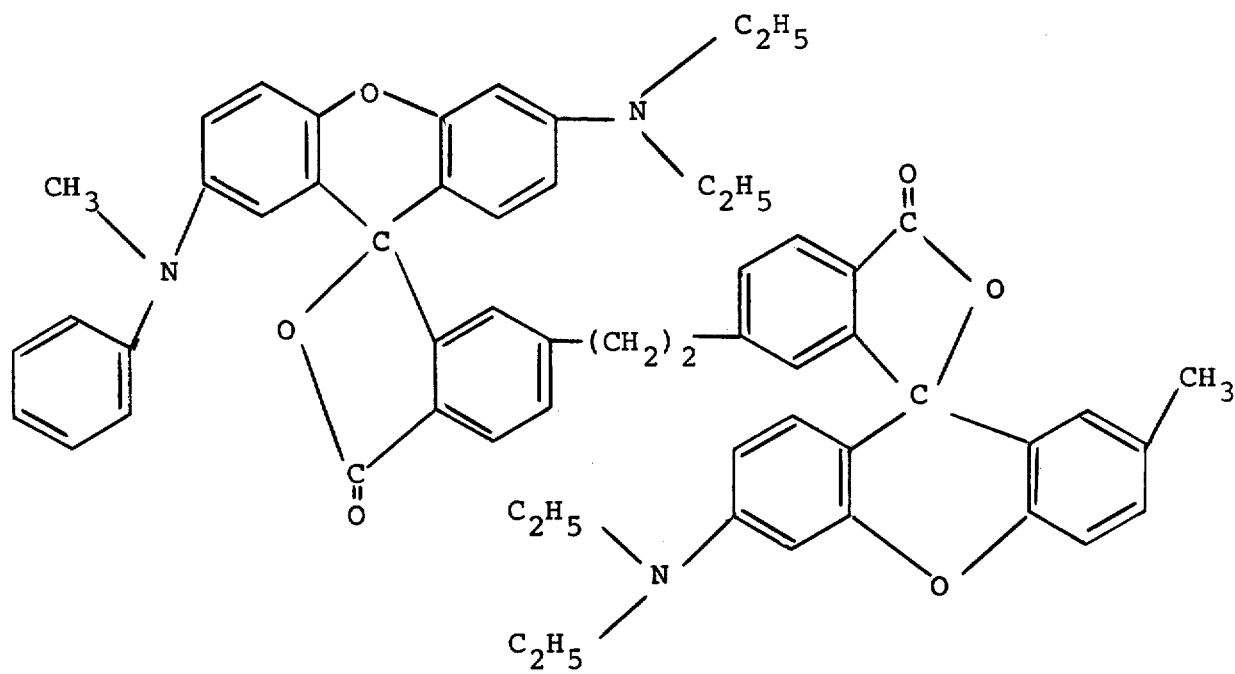

Signed and Sealed this

Sixteenth Day of February 1982

[SEAL]

Attest:

GERALD J. MOSSINGHOFF

Attesting Officer    Commissioner of Patents and Trademarks